United States Patent
Pastore et al.

(10) Patent No.: US 7,742,813 B2
(45) Date of Patent: Jun. 22, 2010

(54) MINIMIZING HEMODYNAMIC COMPROMISE DURING POST-MI REMODELING CONTROL PACING

(75) Inventors: Joseph M. Pastore, Woodbury, MN (US); Rodney W. Salo, Fridley, MN (US); Jesse W. Hartley, Lino Lakes, MN (US); Andrew P. Kramer, Stillwater, MN (US); Jeffrey E. Stahmann, Ramsey, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1068 days.

(21) Appl. No.: 11/276,741

(22) Filed: Mar. 13, 2006

(65) Prior Publication Data
US 2006/0287683 A1    Dec. 21, 2006

Related U.S. Application Data

(60) Provisional application No. 60/678,337, filed on May 6, 2005.

(51) Int. Cl.
*A61N 1/368* (2006.01)
(52) U.S. Cl. .............................. 607/9; 607/17
(58) Field of Classification Search ................. None
See application file for complete search history.

(56) References Cited

U.S. PATENT DOCUMENTS

| | | | |
|---|---|---|---|
| 5,190,035 A | 3/1993 | Salo et al. | |
| 5,749,906 A | 5/1998 | Kieval et al. | |
| 6,161,042 A | 12/2000 | Hartley et al. | |
| 6,628,988 B2 * | 9/2003 | Kramer et al. | 607/9 |
| 7,065,405 B2 * | 6/2006 | Pastore et al. | 607/9 |
| 7,346,394 B2 * | 3/2008 | Liu et al. | 607/18 |
| 7,366,567 B2 * | 4/2008 | Zhu et al. | 607/9 |
| 7,392,084 B2 * | 6/2008 | KenKnight et al. | 607/18 |
| 7,404,802 B2 * | 7/2008 | Siejko et al. | 600/528 |
| 7,450,988 B2 * | 11/2008 | Ross et al. | 607/9 |
| 2004/0230240 A1 | 11/2004 | Sun et al. | |
| 2005/0055058 A1 | 3/2005 | Mower | |
| 2005/0065554 A1 * | 3/2005 | KenKnight et al. | 607/4 |

FOREIGN PATENT DOCUMENTS

| | | |
|---|---|---|
| WO | WO-03/047686 A2 | 6/2003 |
| WO | WO-2006/121845 A2 | 11/2006 |

OTHER PUBLICATIONS

PCT Application No. PCT/US2006/017388 International Search Report and Written Opinion mailed Nov. 16, 2006, 12 pgs.

* cited by examiner

*Primary Examiner*—Kennedy J Schaetzle
(74) *Attorney, Agent, or Firm*—Schwegman, Lundberg & Woessner, P.A.

(57) ABSTRACT

A method and device for delivering pre-excitation pacing to prevent or reduce cardiac remodeling following a myocardial infarction is described. The pre-excitation pacing is modulated in accordance with an assessment of cardiac function in order to balance the beneficial effects of stress reduction with hemodynamic compromise.

18 Claims, 3 Drawing Sheets

MINIMIZING HEMODYNAMIC COMPROMISE DURING POST-MI REMODELING CONTROL PACING

CROSS-REFERENCE TO RELATED APPLICATION(S)

This application claims the benefit of U.S. Provisional Application No. 60/678,337, filed on May 6, 2005, under 35 U.S.C. §119(e), which is hereby incorporated by reference.

FIELD OF THE INVENTION

This patent application pertains to methods and apparatus for the treatment of cardiac disease. In particular, it relates to methods and apparatus for improving cardiac function with electro-stimulatory therapy.

BACKGROUND

A myocardial infarction is the irreversible damage done to a segment of heart muscle by ischemia, where the myocardium is deprived of adequate oxygen and metabolite removal due to an interruption in blood supply. It is usually due to a sudden thrombotic occlusion of a coronary artery, commonly called a heart attack. If the coronary artery becomes completely occluded and there is poor collateral blood flow to the affected area, a transmural or full-wall thickness infarct can result in which much of the contractile function of the area is lost. Over a period of one to two months, the necrotic tissue heals, leaving a scar. The most extreme example of this is a ventricular aneurysm where all of the muscle fibers in the area are destroyed and replaced by fibrous scar tissue.

Even if the ventricular dysfunction as a result of the infarct is not immediately life-threatening, a common sequela of a transmural myocardial infarction in the left ventricle is heart failure brought about by ventricular remodeling. Left ventricular remodeling is a physiological process in response to the hemodynamic effects of the infarct that causes changes in the shape and size of the left ventricle. Remodeling is initiated in response to a redistribution of cardiac stress and strain caused by the impairment of contractile function in the infarcted area as well as in nearby and/or interspersed viable myocardial tissue with lessened contractility due to the infarct. The remodeling process following a transmural infarction starts with an acute phase which lasts only for a few hours. The infarcted area at this stage includes tissue undergoing ischemic necrosis and is surrounded by normal myocardium. Over the next few days and months after scar tissue has formed, global remodeling and chamber enlargement occur in a third phase due to complex alterations in the architecture of the left ventricle involving both infarcted and non-infarcted areas. Remodeling is thought to be the result of a complex interplay of hemodynamic, neural, and hormonal factors.

It has been shown that the extent of ventricular remodeling is positively correlated with increased mortality in post-MI patients. It is with reversing and/or preventing such ventricular remodeling that the present invention is primarily concerned.

SUMMARY

The part of the myocardium that is most vulnerable to the post-infarct remodeling process is the infarct region, which is an area that includes sites in and around the infarct where the myocardial fibers are still intact but contractile function is impaired. The infarct region is thus the area most likely to undergo progressive dilation described above with wall thinning and further impairment of function. By pacing myocardial sites in proximity to the infarct with appropriately timed pacing pulses, the infarct region is pre-excited in a manner that lessens the mechanical stress to which it is subjected, thus reducing the stimulus for remodeling. Pre-excitation of one or more myocardial sites, however, may have an adverse effect on cardiac function by causing less efficient pumping. Described herein is a device and method which provides pre-excitation of myocardial sites to control remodeling in a manner which minimizes hemodynamic compromise.

DETAILED DESCRIPTION

Figure 1:
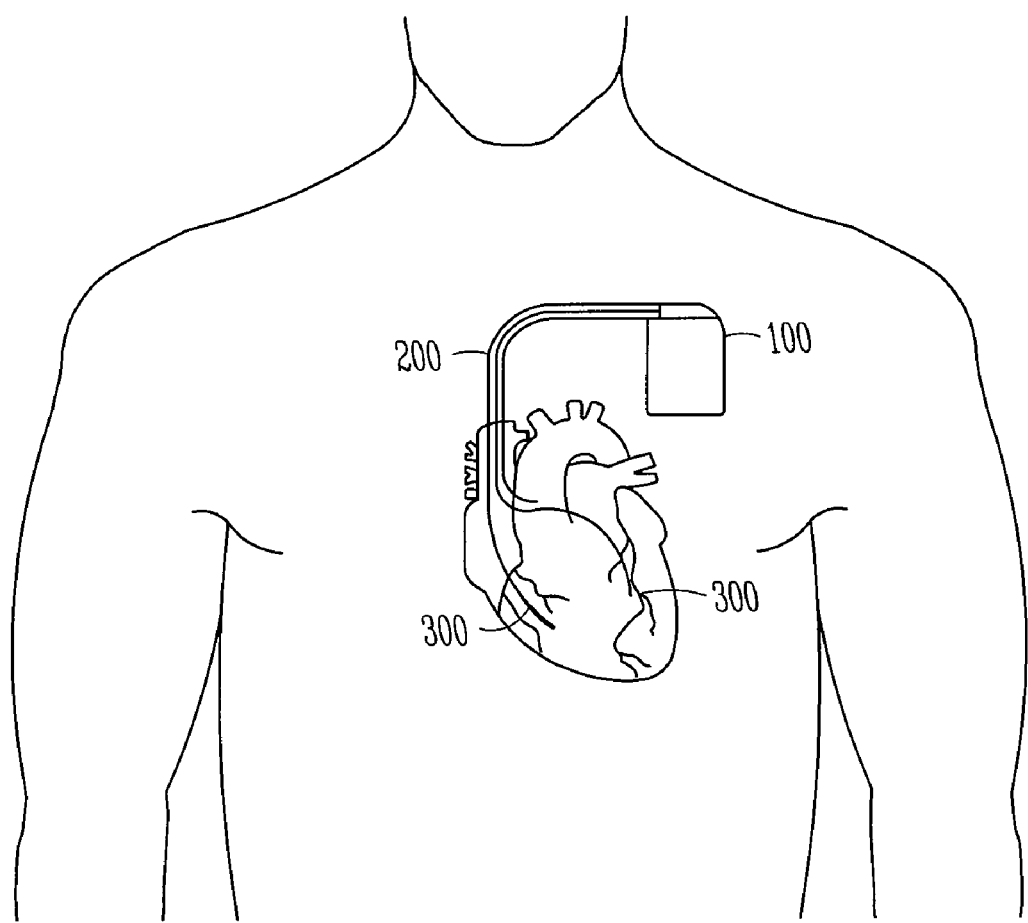
FIG. 1 illustrates the physical placement of an implantable cardiac device.

The degree to which a heart muscle fiber is stretched before it contracts is termed the preload, while the degree of tension or stress on a heart muscle fiber as it contracts is termed the afterload. The maximum tension and velocity of shortening of a muscle fiber increases with increasing preload, and the increase in contractile response of the heart with increasing preload is known as the Frank-Starling principle. When a myocardial region contracts late relative to other regions, the contraction of those other regions stretches the later contracting region and increases its preloading, thus causing an increase in the contractile force generated by the region. Conversely, a myocardial region that contracts earlier relative to other regions experiences decreased preloading and generates less contractile force. Because pressure within the ventricles rises rapidly from a diastolic to a systolic value as blood is pumped out into the aorta and pulmonary arteries, the parts of the ventricles that contract earlier during systole do so against a lower afterload than do parts of the ventricles contracting later. Thus, if a ventricular region can be made to contract earlier than parts of the ventricle, it will be subjected to both a decreased preload and afterload which decreases the mechanical stress experienced by the region relative to other regions during systolic contraction. The region will also do less work thus lessening its metabolic demands and the degree of any ischemia that may be present.

If the region around an infarct were made to contract during early systole, it would be subjected to less distending forces and less likely to undergo expansion, especially during the period immediately after a myocardial infarction. In order to cause early contraction and lessened stress, electro-stimulatory pacing pulses may be delivered to one or more sites in or around the infarct in a manner that pre-excites those sites relative to the rest of the ventricle. (As the term is used herein, a pacing pulse is any electrical stimulation of the heart of sufficient energy to initiate a propagating depolarization, whether or not intended to enforce a particular heart rate.) In a normal heartbeat, the specialized His-Purkinje conduction network of the heart rapidly conducts excitatory impulses from the sino-atrial node to the atrio-ventricular node, and thence to the ventricular myocardium to result in a coordinated contraction of both ventricles. Artificial pacing with an electrode fixed into an area of the myocardium does not take advantage of the heart's normal specialized conduction system for conducting excitation throughout the ventricles because the specialized conduction system can only be entered by impulses emanating from the atrio-ventricular node. Thus the spread of excitation from a ventricular pacing site must proceed only via the much slower conducting ventricular muscle fibers, resulting in the part of the ventricular myocardium stimulated by the pacing electrode contracting well before parts of the ventricle located more distally to the electrode. This pre-excitation of a paced site relative to other sites can be used to deliberately change the distribution of wall stress experienced by the ventricle during the cardiac pumping cycle in order to prevent or reduce the remodeling that would otherwise occur. Pre-excitation of the infarct region relative to other regions unloads the infarct region from mechanical stress by decreasing its afterload and preload, thus preventing or minimizing the remodeling that would otherwise occur. Pacing therapy to unload the infarct region may be implemented by pacing the ventricles at a single site in proximity to the infarct region or by pacing at multiple ventricular sites in such proximity. In the latter case, the pacing pulses may be delivered to the multiple sites simultaneously or in a defined pulse output sequence. As described below, the single-site or multiple site pacing may be performed in accordance with a bradycardia pacing algorithm such as an inhibited demand mode or a triggered mode.

Pre-excitation of a particular myocardial site or sites in order to lessen the mechanical stress to which they are subjected during systole may also, however, have the unfortunate effect of compromising cardiac function. This can come about because pre-excitation of a ventricular region causes that region to contract earlier than other regions, resulting in an asynchronous contraction of the ventricle. Such an asynchronous contraction is less efficient than in the normal situation where all regions of the ventricle contract almost simultaneously. Post-MI patients with already weakened hearts may not tolerate this asynchrony well and exhibit lessened systolic pressure and/or stroke volume. Described herein is a device and method which provides pre-excitation of myocardial sites to control remodeling and which also monitors cardiac function in order to modulate the pre-excitation pacing in a manner which minimizes hemodynamic compromise.

1. Exemplary Device Description

As shown in FIG. 1, an implantable cardiac device 100 for delivering CRT is typically placed subcutaneously or submuscularly in a patient's chest with leads 200 threaded intravenously into the heart to connect the device to electrodes 300 used for sensing and pacing of the atria and/or ventricles. Electrodes may also be positioned on the epicardium by various means. A programmable electronic controller causes the pacing pulses to be output in response to lapsed time intervals and sensed electrical activity (i.e., intrinsic heart beats not as a result of a pacing pulse). The device senses intrinsic cardiac electrical activity through a sensing channel which incorporates internal electrodes disposed near the chamber to be sensed. A depolarization wave associated with an intrinsic contraction of the atria or ventricles that is detected by the device is referred to as an atrial sense or ventricular sense, respectively. In order to cause such a contraction in the absence of an intrinsic beat, a pacing pulse with energy above a certain threshold is delivered to the chamber through a pacing channel which incorporates internal electrodes disposed near the chamber to be paced.

A block diagram of an exemplary pacemaker for delivering pre-excitation pacing therapy to a site or sites in proximity to an infarct as described above is illustrated in FIG. 2. Pacemakers are usually implanted subcutaneously in the patient's chest and connected to sensing/pacing electrodes by leads either threaded through the vessels of the upper venous system to the heart or by leads that penetrate the chest wall. (As the term is used herein, a "pacemaker" should be taken to mean any cardiac rhythm management device with a pacing functionality regardless of any other functions it may perform.) The controller of the pacemaker is made up of a microprocessor 10 communicating with a memory 12 via a bidirectional data bus, where the memory 12 typically comprises a ROM (read-only memory) for program storage and a RAM (random-access memory) for data storage. The controller could be implemented by other types of logic circuitry (e.g., discrete components or programmable logic arrays) using a state machine type of design, but a microprocessor-based system is preferable. The controller is capable of operating the pacemaker in a number of programmed modes where a programmed mode defines how pacing pulses are output in response to sensed events and expiration of time intervals. A telemetry unit 80 is also provided for communicating with an external programmer.

Figure 2:
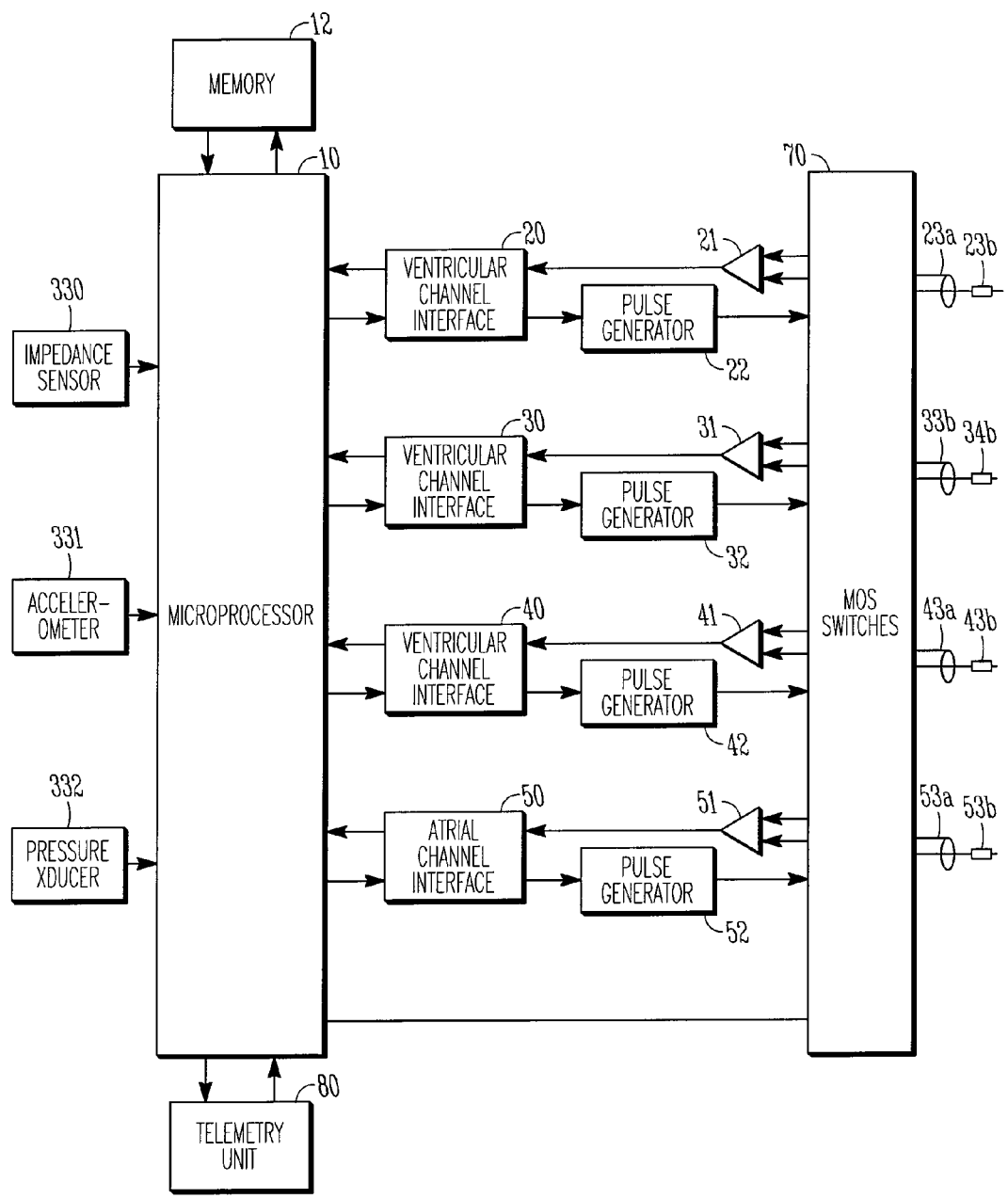
FIG. 2 is a system diagram of a cardiac device configured for multi-site stimulation and sensing.

The device illustrated in FIG. 2 has multiple sensing and pacing channels and is therefore capable of delivering single-site or multiple site ventricular pacing. The multiple sensing and pacing channels may be configured as either atrial or ventricular channels allowing the device to deliver such pacing with or without atrial tracking. Shown in FIG. 2 is a configuration with one atrial sensing/pacing channel and three ventricular sensing/pacing channels. The atrial sensing/pacing channel comprises ring electrode 53a, tip electrode 53b, sense amplifier 51, pulse generator 52, and an atrial channel interface 50 which communicates bidirectionally with a port of microprocessor 10. The three ventricular sensing/pacing channels that include ring electrodes 23a, 33a, and 43a, tip electrodes 23b, 33b, and 43b, sense amplifiers 21, 31, and 41, pulse generators 22, 32, and 42, and ventricular channel interfaces 20, 30, and 40. A pacing channel is made up of the pulse generator connected to the electrode while a sensing channel is made up of the sense amplifier connected to the electrode. The channel interfaces include analog-to-digital converters for digitizing sensing signal inputs from the sensing amplifiers, registers that can be written to for adjusting the gain and threshold values of the sensing amplifiers, and registers for controlling the output of pacing pulses and/or changing the pacing pulse amplitude. In certain patients, pacing of sites in proximity to an infarct or within ischemic regions may be less excitable than normal and require an increased pacing energy in order to achieve capture (i.e., initiating of a propagating action potential). For each channel, the same electrode pair can be used for both sensing and pacing. In this embodiment, bipolar leads that include two electrodes are used for outputting a pacing pulse and/or sensing intrinsic activity. Other embodiments may employ a single electrode for sensing and pacing in each channel, known as a unipolar lead. A MOS switching network 70 controlled by the microprocessor is used to switch the electrodes from the input of a sense amplifier to the output of a pulse generator as well as configure sensing or pacing channels with the available electrodes.

The controller controls the overall operation of the device in accordance with programmed instructions stored in memory. The controller interprets electrogram signals from the sensing channels and controls the delivery of paces in accordance with a pacing mode. The sensing circuitry of the pacemaker generates atrial and ventricular electrogram signals from the voltages sensed by the electrodes of a particular channel. When an electrogram signal in an atrial or sensing channel exceeds a specified threshold, the controller detects an atrial or ventricular sense, respectively, which pacing algorithms may employ to trigger or inhibit pacing.

Pre-excitation therapy is most conveniently delivered in conjunction with a bradycardia pacing mode. Bradycardia pacing modes refer to pacing algorithms used to pace the atria and/or ventricles in a manner that enforces a certain minimum heart rate. For example, a ventricular escape interval for pacing the ventricles can be defined between ventricular events, referred to as the cardiac cycle (CC) interval with its inverse being the lower rate limit or LRL. The CC interval is restarted with each ventricular sense or pace. In atrial tracking and AV sequential pacing modes, another ventricular escape interval is defined between atrial and ventricular events, referred to as the AV delay (AVD) interval, where a ventricular pacing pulse is delivered upon expiration of the AV delay interval if no ventricular sense occurs before. In an atrial tracking mode, the atrio-ventricular pacing delay interval is triggered by an atrial sense and stopped by a ventricular sense or pace. An atrial escape interval can also be defined for pacing the atria either alone or in addition to pacing the ventricles. In an AV sequential pacing mode, the atrio-ventricular delay interval is triggered by an atrial pace and stopped by a ventricular sense or pace. Atrial tracking and AV sequential pacing are commonly combined so that an AVD interval starts with either an atrial pace or sense.

In the case where the pre-excitation pacing of the ventricle is delivered at multiple sites, the sites may be paced simultaneously or in accordance with a particular pulse output sequence that specifies the order in which the sites are to be paced during a single beat. Pre-excitation pacing may involve biventricular pacing with the paces to right and left ventricles delivered either simultaneously or sequentially, with the interval between the paces termed the biventricular offset (BVO) interval (also sometimes referred to as the LV offset (LVO) interval or VV delay). The offset interval may be zero in order to pace both ventricles simultaneously or non-zero in order to pace the left and right ventricles sequentially. As the term is used herein, a negative BVO refers to pacing the left ventricle before the right, while a positive BVO refers to pacing the right ventricle first. As the term is used herein for biventricular pacing, the AVD interval refers to the interval between an atrial event (i.e., a pace or sense in one of the atria, usually the right atrium) and the first ventricular pace which pre-excites one of the ventricles, and the pacing instant for the non-pre-excited ventricle is specified by the BVO interval so that it is paced at an interval AVD+BVO after the atrial event. With either biventricular or left ventricle-only pacing, the AVD interval may be the same or different depending upon whether it is initiated by an atrial sense or pace (i.e., in atrial tracking and AV sequential pacing modes, respectively). A common way of implementing biventricular pacing or left ventricle-only pacing is to base the timing upon only right ventricular activity so that ventricular escape intervals are reset or stopped by right ventricular senses.

2. Assessment of Cardiac Function

In order to minimize or lessen hemodynamic compromise resulting from pre-excitation pacing, the delivery of such pacing may be modulated in accordance with an assessment of cardiac function. One or more additional sensing modalities may be incorporated into the implantable device for this purpose, where the additional sensors are interfaced to the microprocessor 10. Cardiac output may be measured by an impedance technique in which transthoracic impedance is measured and used to compute stroke volume. An impedance sensor 330 includes an exciter and an impedance measuring circuit. Processing of the impedance signal allows the derivation of a signal representing respiratory activity and/or cardiac blood volume, depending upon the location of the voltage sense electrodes in the thorax. (See, e.g., U.S. Pat. Nos. 5,190,035 and 6,161,042, assigned to the assignee of the present invention and hereby incorporated by reference.) If the electrodes are located so as to measure impedance across the lungs, the patient's minute ventilation may be derived from the respiratory activity signal and may be used as an indication of exertion level. If the electrodes are located to measure impedance across the heart, the impedance signal is filtered to remove the respiratory component, the result is a signal that is representative of blood volume in the heart at any point in time, thus allowing the computation of stroke volume and, when combined with heart rate, computation of cardiac output. The stroke volume integrated over time (or averaged and multiplied by heart rate) gives the patient's cardiac output. The impedance technique for measuring cardiac output discussed above may also be used to measure ventricular volumes at various stages of the cardiac cycle such as end-diastolic and end-systolic volumes and used to compute parameters reflective of cardiac function such as ejection fraction. The implantable device may also be equipped with other sensing modalities such as a pressure transducer 332. Such a pressure transducer may be attached to an intravascular lead and be appropriately disposed for measuring diastolic filling pressures and/or systolic pulse pressures.

Any or all of the parameters related to cardiac function described above may be used to derive a cardiac function assessment, where the assessment may simply be a cardiac function parameter (e.g., cardiac output) or a function of one or more such parameters. One such function incorporates one or more cardiac function parameters along with a measurement of the patient's exertion level. For example, cardiac function may be assessed by measuring both cardiac output and the patient's exertion level. Exertion level may be measured with an impedance sensor configured to measure minute ventilation as described above, with an accelerometer 331 for measuring physical activity level, or heart rate if the patient is chronotropically competent. A look-up table or other function may be used to compute what cardiac output is considered adequate for a given exertion level, referred to as cardiac output demand. The cardiac function assessment may then take the form of a numerical value that reflects both cardiac output and the patient's exertion level (e.g., the difference or ratio between the measured cardiac output and cardiac demand). The value of the cardiac function assessment in this case then varies in accordance with the adequacy of the patient's cardiac output as determined by the measured exertion level. As discussed below, the cardiac function assessment may then be compared with specified threshold values with the delivery of pre-excitation pacing modulated in accordance with the result. Alternatively, a ratio of the extent of pre-excitation pacing to the cardiac function assessment may be computed from numerical values related to pre-excitation pacing and the cardiac function assessment, respectively. The delivery of pre-excitation pacing may then be modulated in a manner that maintains the ratio within a specified range.

3. Exemplary Implementation

In an exemplary embodiment, an implantable device for delivering cardiac therapy to post-MI patients includes one or more pacing channels for delivering pacing pulses to one or more ventricular sites. The controller is programmed to deliver pacing which pre-excites a region of the ventricular myocardium so as to mechanically unload that region during systole. The therapy may be delivered as single-site pacing, biventricular pacing where one of the ventricles is pre-excited relative to the other as determined by a programmed biventricular offset interval, or delivered as multi-site ventricular pacing where at least one of the ventricles is paced at a plurality of sites so as to pre-excite one or more of the sites relative to the other sites. In any case, the ventricular pacing may be delivered in a non-atrial tracking mode where a ventricular escape interval is defined between ventricular paces, or in an atrial tracking mode where the ventricular paces are delivered after a defined atrio-ventricular escape interval following an atrial sense. In a patient who is chronotropically incompetent, an atrial pacing channel may also be provided for pacing the atria, with the ventricular pace(s) delivered upon expiration of the atrio-ventricular escape interval following the atrial pace.

Figure 3:
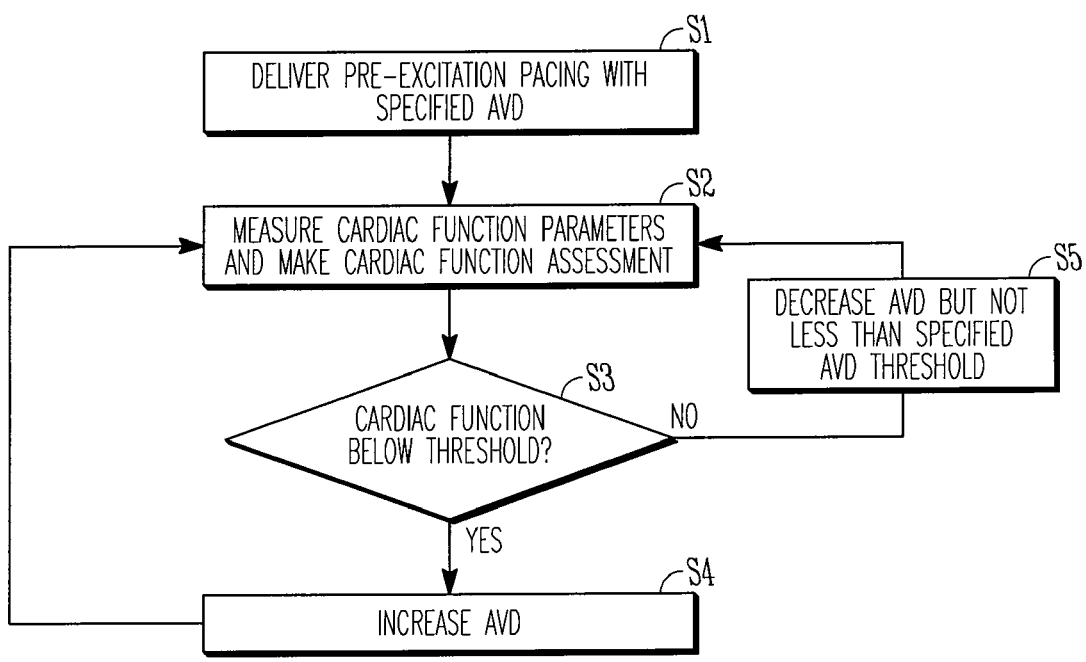
FIG. 3 illustrates an exemplary algorithm for modulating pre-excitation pacing.

In pre-excitation pacing using an atrial tracking mode, the parameter that determines the amount of pre-excitation is the AV delay or AVD. Delivering electrical pacing therapy near an infarct region can reduce wall stress in that region to the extent that the region contracts before other regions contract due to intrinsic activation, and that the effect is dependent on AV delay. As paced AV delay shortens, the size of the region that is unloaded is increased, and the absolute amount of unloading in the region (as measured by a decrease in regional stroke work) is increased. However, as AV delay shortens, cardiac function is reduced. Therefore, the amount of unloading produced by pre-excitation pacing and cardiac function are inversely related. In order to provide a balance between the amount of unloading and the compromise of cardiac function, the device is programmed to provide a closed-loop system for ensuring that cardiac function is not overly compromised. FIG. 3 illustrates an exemplary algorithm which may be performed by a microprocessor and/or other circuitry as steps S1 through S5, executed serially or concurrently. The device is programmed to deliver pre-excitation pacing with a specified AVD at step S1 while monitoring cardiac function using one or more of the techniques described above at step S2. If cardiac function falls below a specified threshold as determined at step S3, the device increases the AVD at step S4. The device may also decrease the AVD at step S5 if cardiac function exceeds a specified threshold. Either instead of, or in addition to changing the AVD in response to a cardiac function assessment, the device could automatically adjust the BVO or other offset to result in more or less pre-excitation, change the pacing site or sites, or cease or initiate pre-excitation pacing therapy.

In another embodiment, the device is programmed to calculate a specific ratio between the extent of unloading and cardiac function. The delivery of pre-excitation pacing is then made to vary in a manner that attempts to maintain within a specified range the ratio of a parameter related to the amount pre-excitation pacing (i.e., the amount of regional unloading as derived from pre-excitation parameters such as AVD and BVO) to a parameter related to the cardiac function assessment. By maintaining the ratio within a specified range, the device matches cardiac output to patient metabolic need as estimated by exertion level. As the patient exercises, and cardiac output demand increases, the device increase AV delay (or adjusts other pre-excitation parameters) to reduce unloading and maximize cardiac output. When exertion is reduced, the device shortens the AV delay (or adjusts other pre-excitation parameters) to restore more regional unloading for a given cardiac output level. Either in addition or instead of using pre-excitation parameters to reflect the extent of unloading, the extent of unloading brought about by the pre-excitation pacing could be measured by an ultrasonic transducer connected to an intravascular lead for measuring wall thickness or by an impedance technique for determining mechanical activation time, or a local strain gauge connected to a cardiac lead (or implanted separately) for measuring regional stress.

Although the invention has been described in conjunction with the foregoing specific embodiments, many alternatives, variations, and modifications will be apparent to those of ordinary skill in the art. Such alternatives, variations, and modifications are intended to fall within the scope of the following appended claims.

What is claimed is:

1. An implantable device for delivering cardiac therapy to a patient, comprising:
   one or more pacing channels for delivering pacing pulses to one or more ventricular sites;
   a sensor for measuring a parameter related to cardiac function;
   a controller for controlling the delivery of pacing pulses to one or more ventricular sites during a cardiac cycle in accordance with a programmed pacing mode;
   wherein the controller is programmed to deliver pre-excitation pacing which pre-excites a region of the ventricular myocardium so as to mechanically unload that region during systole; and,
   wherein the controller is further programmed to derive a cardiac function assessment from the measured cardiac function parameter and modulate the amount of pre-excitation pacing in accordance therewith, wherein the controller is programmed to reduce the amount of pre-excitation pacing if the cardiac function assessment is below a specified threshold value.

2. The device of claim 1 wherein the controller is programmed to increase the amount of pre-excitation pacing if the cardiac function assessment is above a specified threshold value.

3. The device of claim 1 wherein the controller is programmed to modulate the amount of pre-excitation pacing by adjusting an AV delay of an atrial tracking mode.

4. The device of claim 1 wherein the controller is programmed to modulate the amount of pre-excitation pacing by changing a biventricular offset of a biventricular pacing mode.

5. The device of claim 1 wherein the controller is programmed to modulate the amount of pre-excitation pacing by changing a pacing site.

6. The device of claim 1 wherein the controller is programmed to modulate the amount of pre-excitation pacing by initiating or ceasing pre-excitation pacing.

7. The device of claim 1 wherein the sensor for measuring a parameter related to cardiac function is an impedance sensor for measuring stroke volume.

8. The device of claim 1 wherein the sensor for measuring a parameter related to cardiac function measures cardiac output and wherein the controller is programmed to derive the cardiac function assessment from the measured cardiac output and a measured exertion level.

9. A method for delivering cardiac therapy to a patient, comprising:
   delivering pacing pulses to one or more ventricular sites as pre-excitation pacing which pre-excites a region of the ventricular myocardium so as to mechanically unload that region during systole;
   measuring a parameter related to cardiac function; and,
   deriving a cardiac function assessment from the measured cardiac function parameter and modulate the amount of pre-excitation pacing in accordance therewith by reducing the amount of pre-excitation pacing if the cardiac function assessment is below a specified threshold value.

10. The method of claim 9 further comprising increasing the amount of pre-excitation pacing if the cardiac function assessment is above a specified threshold value.

11. The method of claim 9 further comprising modulating the amount of pre-excitation pacing by adjusting an AV delay of an atrial tracking mode.

12. The method of claim 9 further comprising modulating the amount of pre-excitation pacing by changing a biventricular offset of a biventricular pacing mode.

13. The method of claim 9 wherein further comprising modulating the amount of pre-excitation pacing by changing a pacing site.

14. The method of claim 9 further comprising modulating the amount of pre-excitation pacing by initiating or ceasing pre-excitation pacing.

15. The method of claim 9 further comprising measuring a parameter related to cardiac function with an impedance sensor for measuring stroke volume.

16. The method of claim 9 further comprising measuring a parameter related to cardiac function by measuring cardiac output and deriving the cardiac function assessment from the measured cardiac output and a measured exertion level.

17. An implantable device for delivering cardiac therapy to a patient, comprising:
   one or more pacing channels for delivering pacing pulses to one or more ventricular sites;
   a sensor for measuring a parameter related to cardiac function;
   a controller for controlling the delivery of pacing pulses to one or more ventricular sites during a cardiac cycle in accordance with a programmed pacing mode;
   wherein the controller is programmed to deliver pre-excitation pacing which pre-excites a region of the ventricular myocardium so as to mechanically unload that region during systole; and,
   wherein the controller is further programmed to derive a cardiac function assessment from the measured cardiac function parameter and modulate the amount of pre-excitation pacing in accordance therewith, wherein the controller is programmed to maintain within a specified range a ratio of cardiac function to pre-excitation pacing.

18. A method for delivering cardiac therapy to a patient, comprising:
   delivering pacing pulses to one or more ventricular sites as pre-excitation pacing which pre-excites a region of the ventricular myocardium so as to mechanically unload that region during systole;
   measuring a parameter related to cardiac function; and,
   deriving a cardiac function assessment from the measured cardiac function parameter and modulating the amount of pre-excitation pacing in accordance therewith by maintaining within a specified range a ratio of cardiac function to pre-excitation pacing.

* * * * *